United States Patent [19]
Guala

[11] Patent Number: 6,086,762
[45] Date of Patent: Jul. 11, 2000

[54] TRANSDUCER-PROTECTOR DEVICE FOR BIOMEDICAL HAEMODIALYSIS LINES

[75] Inventor: Gianni Guala, Turin, Italy

[73] Assignee: Industrie Borla S.p.A., Turin, Italy

[21] Appl. No.: 09/105,053

[22] Filed: Jun. 26, 1998

[30] Foreign Application Priority Data

Jun. 27, 1997 [IT] Italy .................................. TO97A0565

[51] Int. Cl.⁷ .................................................. B01D 29/00
[52] U.S. Cl. .......................... 210/232; 210/445; 210/446
[58] Field of Search .................................... 210/445, 446, 210/451, 453, 455, 232, 454; 604/126, 252

[56] References Cited

U.S. PATENT DOCUMENTS

| | | | |
|---|---|---|---|
| 3,658,183 | 4/1972 | Best et al. ................................ | 210/446 |
| 4,664,800 | 5/1987 | Raines et al. ............................ | 210/451 |
| 5,500,003 | 3/1996 | Guala et al. ............................. | 604/252 |

FOREIGN PATENT DOCUMENTS 0652018  5/1995  European Pat. Off. .

*Primary Examiner*—John Kim
*Attorney, Agent, or Firm*—Sughrue, Mion, Zinn, Macpeak & Seas, PLLC

[57] ABSTRACT

Transducer-protector device for biomedical haemodialysis lines, comprising a first tubular connector of the female Luer Lock type and a second tubular connector which are coaxial to each other and provided with a first and a second annular radial flange, respectively, for their mutual permanent sealed connection by ultrasonic welding, and a filtering membrane interposed and clamped between the first and second annular flanges. The second tubular connector with the second annular flange is formed in one piece of high rigidity molded thermoplastic material, while the first tubular connector with the first annular flange is formed in one piece of a molded thermoplastic material having higher elasticity characteristics, conveniently selected in the class of polybutylenterephthalate polymers.

7 Claims, 3 Drawing Sheets

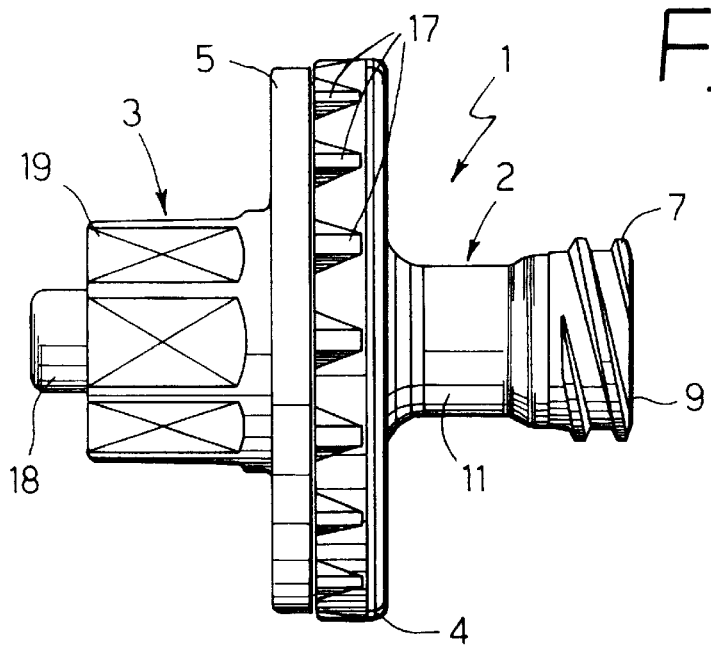
Fig_1
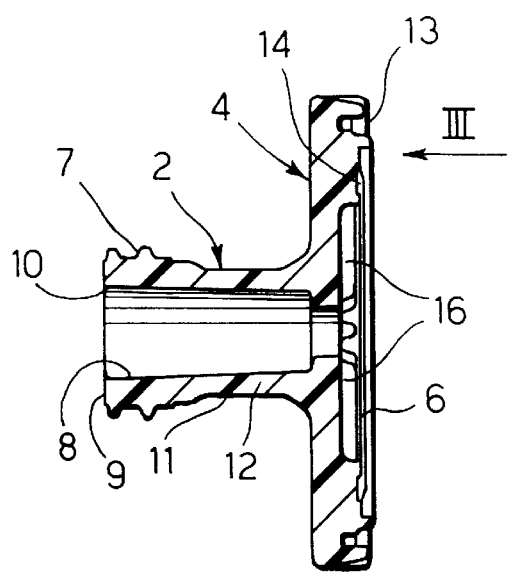
Fig_2
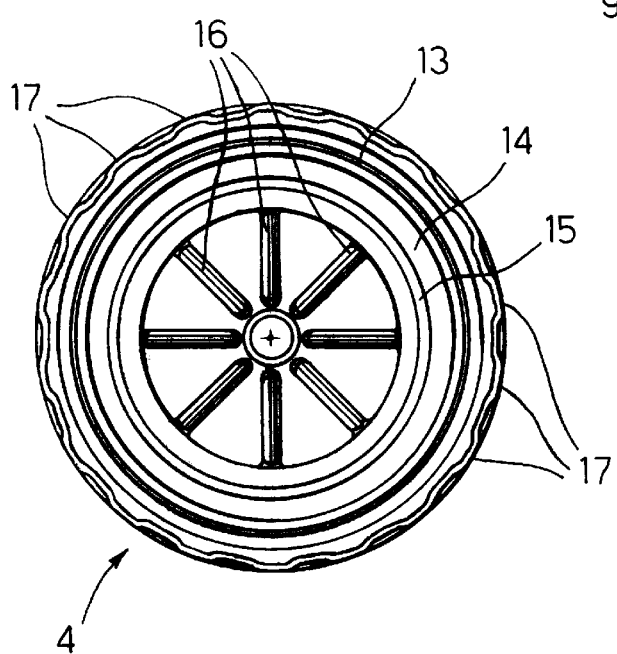
Fig_3

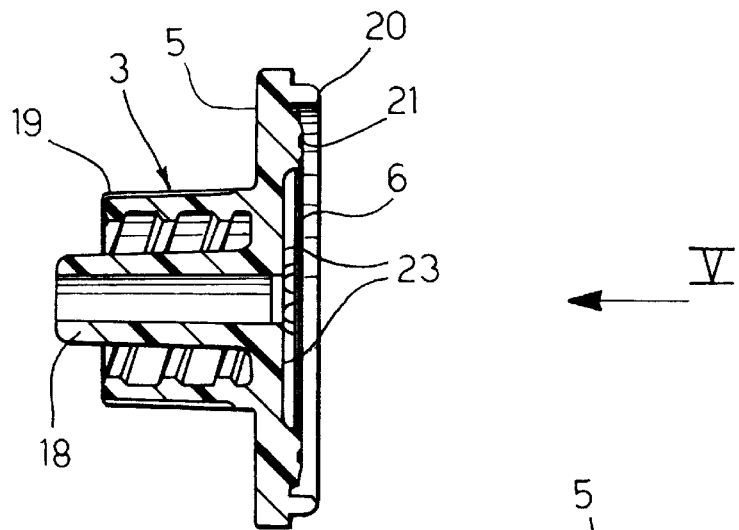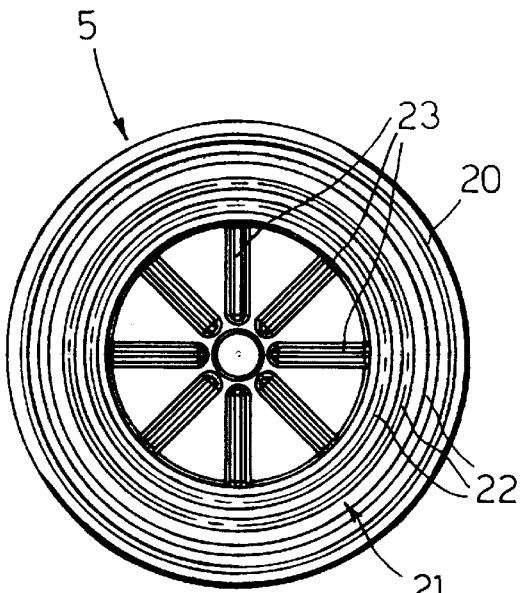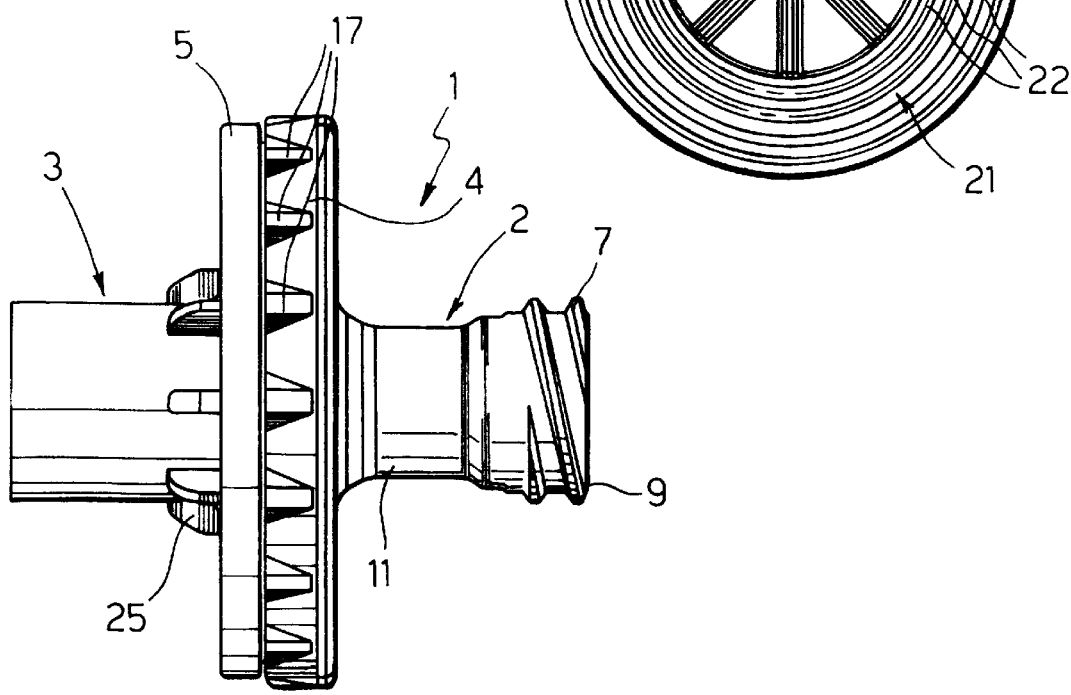

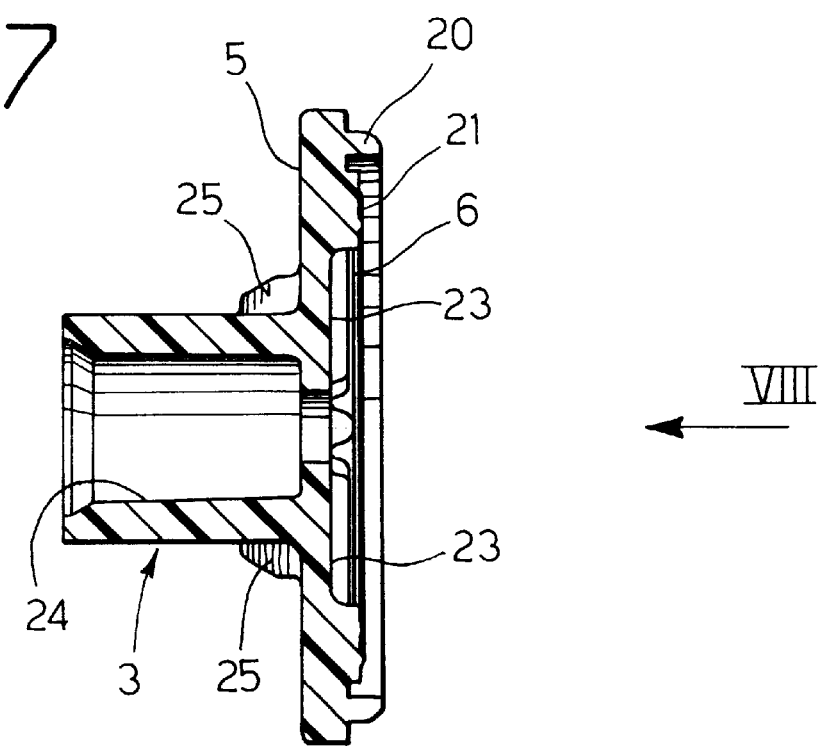
Fig_7
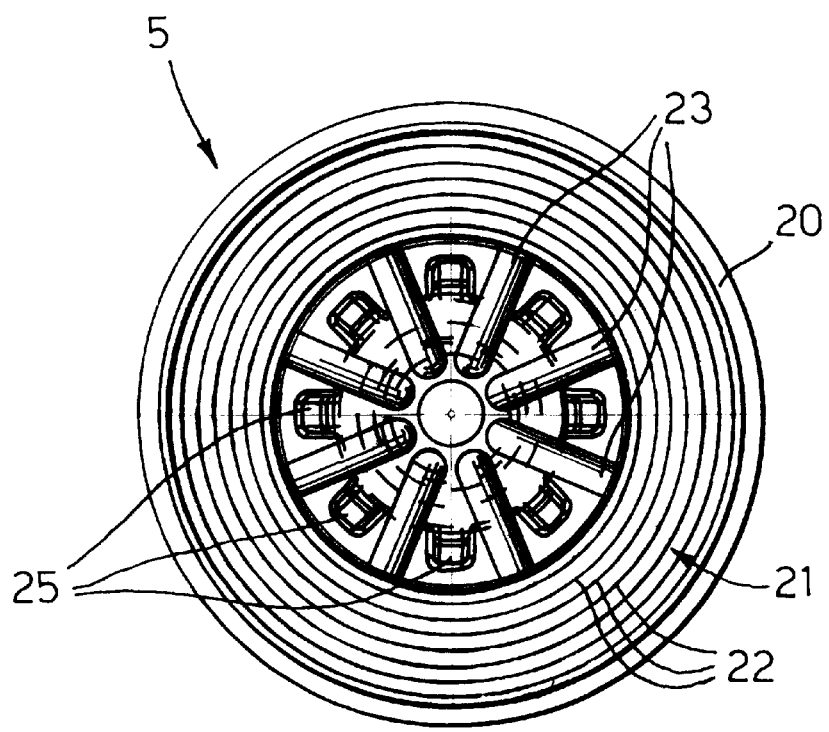
Fig_8

TRANSDUCER-PROTECTOR DEVICE FOR BIOMEDICAL HAEMODIALYSIS LINES

BACKGROUND OF THE INVENTION

The present invention is related to transducer-protector devices for biomedical haemodialysis lines, comprising a first tubular connector of the female Luer Lock type with a conical inner surface and an outer threading, intended to be connected to a tube of a haemodialysis equipment, a second tubular connector coaxial to the first tubular connector, said first and second tubular connectors being provided with respective first and second annular radial flanges for their mutual permanent sealed connection by ultrasonic welding, and a filtering membrane made of a permeable material defining an anti-contamination sterile barrier interposed transversely between said first and second tubular connectors and having a peripheral edge clamped between said annular flanges.

These transducer-protector devices must fulfill two fundamental requirements: firstly they have to warrant in use a perfect and total hermetic tightness between the first tubular connector and the tube of the haemodialysis equipment on one side, and between the second tubular connector and the line connected to the patient on the other side. Secondly they must be capable to ensure their sterilization by means of any traditional system, namely by vapour treatment. Due to this reason the plastic material of which the first and the second radial connecting flanges are formed must be provided with characteristics such as to ensure the necessary structural and dimensional stability even in case of heating up to the vapour sterilizing temperature. Otherwise any deformations of one and/or the other radial flange might cause a non complete locking of the peripheral edge of the filtering membrane clamped between the two flanges and, as a consequence, inefficiency of the sterile barrier which such membrane must instead absolutely provide.

Due the above reason the second tubular connector with the related second annular flange is as a rule formed by one single piece of a moulded high rigidity thermoplastic material, normally polycarbonate.

On the other hand the connection between the first tubular connector of the female Luer Lock type and the tube of the haemodialysis equipment is as a rule carried out through a metallic connector of the male Luer type, joined to the tube. This connection must be perfectly hermetic, and any even slight imperfections may result in a leakage of fluid which is absolutely unacceptable. Due to this reason, use for the manufacturing of the first tubular connector together with the related first radial flange of a high rigidity thermoplastic material, for instance the same material employed for the manufacturing of the second tubular connector with the related second annular flange, which would be desirable to withstand the sterilization process of the transducer-protector device, is not envisageable.

In order to solve this problem solutions have been provided according to which the first annular flange is manufactured with the said high rigidity thermoplastic material, while the first tubular connector of the female Luer Lock type is partially or entirely manufactured with a material having higher elasticity characteristics, so as to warrant perfect hermetic tightness with the metal Luer connector of the haemodialysis equipment.

According to a first known solution, disclosed in Italian patent application No. TO93A000368 in the name of the same Applicant, the conical inner surface of the first tubular connector is formed by an insert made of a plastic material having high elasticity performance, for instance polyester or the like. Such an insert is arranged coaxially within the first tubular connector and is mechanically secured thereto.

According to a second solution, known from European Patent EP-B-0652018 also in the name of the same Applicant, the entire first tubular connector is made of said material having greater elasticity characteristics, and is provided with an axially inner attachment portion fixedly coupled by overmoulding onto a complementary outer axial attachment part of the related first radial flange.

The above known solutions, though quite efficient, have a drawback in that the method for their manufacturing is relatively complex and expensive. Actually in both cases the component elements of the transducer-protector device are three, further to the filtering membrane.

SUMMARY OF THE INVENTION

The object of the present invention is to overcome the above inconveniece and, more particularly, to avoid the two-piece construction of the first tubular connector and related first radial flange, while ensuring in use the necessary coupling precision between the first tubular connector and the tube of the haemodialysis equipment.

According to the invention, this object is achieved by virtue of the fact that said first Luer Lock connector with said first annular flange is constituted by one single piece of moulded thermoplastic material having elasticity characteristics higher than those of said second tubular connector with said second annular flange.

The invention is based on overcoming the technical prejudice according to which relatively elastic thermoplastic materials are generally not suitable to provide a permanent connection by ultrasound welding together with high rigidity thermoplastic materials such as polycarbonate. In this connection, the Applicant has surprisingly ascertained that a particular class of such relatively elastic thermoplastic materials is instead perfectly suitable for joining by ultrasound welding to polycarbonate. In particular, this class consists of polymers of polybutylenterephthalate, and more particularly the one named VESTODUR-X4159 produced and marketed by Hüls. This material, in spite of its relative elasticity which ensures in use a perfectly hermetic joint between the first tubular connector and the metal connector of the haemodialysis equipment tube, is additionally capable to warrant the necessary structural stability of the first annular flange even under high temperature, i.e. even in case of vapour sterilization of the transducer-protector device.

To the aim of further enhancing this structural stability degree, the first annular flange has conveniently an axial thickness substantially greater than the axial thickness of the second annular flange.

According to a preferred embodiment of the invention, the axially outer end of the inner conical surface of the first tubular connector may be innerly formed with an annular radial narrowing.

By virtue of this feature, when in use the metal male Luer connector of the haemodialysis equipment is coupled with the first tubular connector of the transducer-protector device, a forcing effect is provided between the axially outer end of the inner conical surface of the first tubular connector and said metal connector, which ensures a more firm and steady connection therebetween thus eliminating any risks of leakage.

Conveniently the first tubular connector has a differentiated wall thickness, with a first axial portion substantially comprised between the first annular flange and said outer threading, having a smaller wall thickness, and a second axial portion substantially corresponding to said outer threading and to said axially outer end, having a greater wall thickness, and said annular radial narrowing is determined by a different thermal shrinkage of said first and second axial portions following moulding of the first tubular connector with said first annular flange.

Due to this idea of solution, forming the annular radial narrowing of the axially outer end of the first tubular connector conical surface does not require any particular expendient or complication in the moulding apparatus. In practice, following extraction of the first tubular connector and the related first annular flange from the forming mould, the first axial portion having a smaller wall thickness is subjected to shrinkage and stabilization more quickly, and thus earlier than the second axial portion having a greater wall thickness. The subsequent shrinkage of the latter determines as a consequence a slight radial contraction deformation thereof in correspondance of the axially outer end of the inner conical surface of the first tubular connector, which thus produces said inner annular narrowing.

Practically the transducer-protector device according to the invention enables achieving the same advantageous effects of the known solution previously disclosed, leading however to reduce the number of its component elements to two, of course further to the filtering membrane, with an evident semplification and reduction of the manufacturing costs.

BRIEF DESCRIPTION OF THE DRAWINGS

The invention will now be disclosed in detail with reference to the accompanying drawings, purely provided by way of non limiting example, in which:

FIG. 1 is a diagrammatic lateral elevational view of a transducer-protector device according to a first embodiment of the invention, FIG. 2 is an axially sectioned view of a part of the transducer-protector device of FIG. 1, FIG. 3 is a front elevational view according to arrow III of FIG. 2, FIG. 4 is an axially sectioned view of the other part of the transducer-protector device of FIG. 1, FIG. 5 is a front elevational view according to arrow V of FIG. 4, FIG. 6 is a view similar to FIG. 1 of a second embodiment of the transducer-protector device according to the invention, FIG. 7 is an axially sectioned view of the part of the transducer-protector device of FIG. 6 corresponding to the part shown in FIG. 4, and FIG. 8 is a front elevational view according to arrow VIII of FIG. 7.

DETAILED DESCRIPTION OF THE INVENTION

Referring initially to FIGS. 1 through 5, reference numeral 1 generally designates a tranducer-protector device according to the invention, designed to be inserted within a biomedical haemodialysis line.

The transducer-protector device 1 comprises a first tubular connector 2, intended to be connected in use to a tube of a haemodialysis apparatus, and a second tubular connector 3 intended to be connected in use to a tube leading to a patient undergoing haemodialysis.

The first tubular connector 2 is integrally formed with a radial annular flange 4, and the second tubular connector 3 is integrally formed with a radial annular flange 5. The two annular flanges 4,5 are coupled to each other frontally, with the tubular connectors 2,3 arranged coaxially, by virtue of the arrangement disclosed in the following, and are mutually connected in a permanent and sealed fashion by ultrasonic welding.

A filtering membrane 6 made of a permeable material (FIGS. 2 and 4) is interposed between the annular flanges 4,5 with its peripheral outer edge mechanically clamped between corresponding front clamping surfaces of the two annular flanges 4,5, provided radially innerly with respect to the areas thereof mutually joined to each other by ultrasonic welding.

The membrane 6 defines an anti-contamination sterile barrier between the tubular connectors 2 and 3.

Referring now in better detail to FIGS. 2 and 3, according to the fundamental feature of the invention the first tubular connector 2 and the related annular flange 4 are formed integrally by moulding of a thermoplastic material having on one side relatively high elasticity features, and on the other side high structural and dimensional stability features from the thermal point of view, i.e. even in case of heating thereof up to vapour sterilization temperature of the transducer-protector device 1. Moreover the thermoplastic material by which the first tubular connector 2 and the related annular flange 4 are formed is provided with the additional characteristic of being capable to be ultrasonically welded with a thermoplastic material having high resistence and high rigidity such as that, particularly polycarbonate, by which the second tubular connector 3 with the related annular flange 5 is formed.

The Applicant has surprisingly ascertained that the thermoplastic material embodying all the above-listed characteristics belongs to the class of polybutylenterephthalate (PBT) polymers, and consists more particularly of VESTODUR-X4159 produced and marketed by Hüls.

The first tubular connector 2 is formed with an outer threading 7 and with an inner conical surface 8 diverging towards the outer end of the connector 2, indicated as 9. The connector 2 is thus of the female Luer Lock type and is designed to be coupled with a connector of the male Luer Lock type associated to the tube of the haemodialysis equipment.

According to another feature of the invention, the inner conical surface 8 of the first tubular connector 2 is conveniently formed interiorly, in proximity of the axially outer end 9, with a slight annular narrowing indicated as 10. The diameter reduction of this narrowing 10 with respect to the nominal value of the outer end 9 is of the order of a few millimeters/100.

The annular radial narrowing 10 may be obtained, upon moulding of the first tubular connector 2 with the related annular flange 4, by means of technological expedients provided within the forming mould, which are within the skill of the practitioner. However, according to a preferred embodiment, the invention provides that said annular radial narrowing 10 is obtained by forming the tubular connector 2 with a differentiated wall thickness, taking advantage of consequent effects of differentiated thermal shrinkage of the thermoplastic material following the injection moulding process.

Accordingly, the first tubular connector 2 has a first axial portion 11, substantially comprised between the radial flange 4 and the outer threading 7, having a smaller thickness wall, followed by a second axial portion 12, substantially corresponding to the outer threading 7 and to the axially outer end 9, having a greater wall thickness.

By virtue of this arrangement, upon extraction of the tubular connector 2 from the injection mould, the axial portion 11 having a smaller wall thickness cools more quickly, thus shrinking and setting earlier than the axial portion 12 having a greater wall thickness. The slower cooling and thus the later shrinkage of this axial portion 12, in combination with the circumstance that the other axial portion 11 is already set, produces as a consequence a certain degree of radial deformation towards the interior of the area corresponding to the outer free end 9 and, consequently, generation of the annular narrowing 10.

The radial flange 4 is provided with a substantial axial thickness and a generally smaller diameter with respect to the case of the conventional transducer-protector devices. This annular flange 4 is formed frontally with a radially outer annular groove 13 and, innerly of the latter, with an annular retaining surface 14, possibly provided with at least one annular projection 15, for clamping the circumferential edge of the membrane 6. Innerly of the annular retaining surface 14, the front wall of the annular flange 4 is formed with a series of radial ribs 16 against which the membrane 6 is bearing. Moreover the lateral wall of the annular flange 4 is provided with a crown of indentations 17 defining a knurling to make grasping and handling of the transducer-protector device 1 in use more convenient.

Referring now to FIGS. 4 and 5, as previously explained, the second tubular connector 3 and the related annular flange 5 are integrally formed by moulding of a thermoplastic material having a higher resistance and a higher rigidity, normally polycarbonate.

In the case of the embodiment which is now being disclosed, the second tubular connector 3 is formed as a connector of the male Luer Lock type, with an inner tubular portion 18 and an outer hollow cylindrical bush 19 which is innerly threaded.

The annular flange 5, whose axial thickness is smaller than that of the annular flange 4, is formed frontally with a radially outer annular projection 20, designed to fit into the annular groove 13 of the first flange 4, with a radially inner annular retaining surface 21, complementary to the clamping surface 14 of the first flange 4 and possibly provided with a series of annular concentric projection 22 for clamping the outer perimetral edge of the membrane 6, and with a numeber of radial ribbs 23, complementary to the radial ribbs 16 of the first annular flange 4, against which the membrane 6 is bearing.

As clarified in the above, assemblying between the first tubular connector 2 with the first annular flange 4 and the second tubular connector 3 with the second annular flange 5 is performed, following interposition therebetween of the membrane 6 and engagement of the latter between the annular projection 20 and the annular groove 13 of the flange 5 and of the flange 4, respectively, by means of ultrasonic welding. The peripheral edge of the membrane 6 is not interested by the ultrasound welding, and is merely mechanically clamped between the retaining surfaces 14 and 21 of the annular flanges 4,5.

FIGS. 6 through 8 show a variant of the transducer-protector device 1 according to the invention, which differs from the embodiment previously disclosed with reference to FIGS. 1 through 5 only in connection with the configuration of the second tubular connector 3 with the related annular flange 5, while the arrangement of the first tubular connector 2 with the related annular flange 4 is almost identical to the one disclosed in the above.

According to this variant, whose parts identical or similar to those already previously disclosed are indicated by the same reference numerals, the second tubular connector 3 is simply constituted by a cylindrical body having a conical inner surface 24, diverging outwardly, for connection to a tube. Between the outer wall of the tubular connector 3 and the rear wall of the annular flange 5 a crown of integral stiffening radial wings 25 is provided.

Naturally, the details of construction and the emodiment may be widely varied with respect to what has been disclosed and illustrated, without thereby departing from the scope of the present invention, such as defined in the appended claims.

What is claimed is:

1. A tranducer-protector device for biomedical heamodialysis lines, comprising a first tubular connector of the female Luer Lock type with a conical inner surface and an outer threading, intended to be connected to a tube of a haemodialysis equipment, a second tubular connector coaxial to said first tubular connector, said first and second tubular connectors being provided with respective first and second radial annular flanges for their mutual permanent sealed connection by ultrasonic welding, and a filtering membrane made of a permeable material defining an anti-contamination sterile barrier interposed transversely between said first and said second tubular connectors and having a peripheral edge clamped between said radial annular flanges, wherein said second tubular connector with said second radial annular flange is formed by one piece of high rigidity moulded thermoplastic material, and wherein said first Luer Lock connector with said first radial annular flange is constituted by one piece of a moulded thermoplastic material having elasticity characteristics higher than those of said second tubular connector with said second radial annular flange.

2. Device according to claim 1, wherein said thermoplastic material having higher elasticity characteristics is selected in the class of polybutylenterephthalate polymers.

3. Device according to claim 1, wherein said first radial annular flange has an axial thickness substantially greater than the axial thickness of said second radial annular flange.

4. Device according to claim 1, wherein said first and second radial annular flanges have respective radially outer front perimetral portions of mutual axial compenetration and respective radially inner front perimetral surfaces for mechanically clamping said peripheral edge of said filtering membrane.

5. Device according to claim 1, wherein said conical inner surface of said first tubular connector has an axially outer end innerly formed with an annular radial narrowing.

6. Device according to claim 5, wherein said tubular connector has a differentiated wall thickness, with a first axial portion substantially comprised between said first radial annular flange and said outer threading, having a smaller wall thickness, and a second axial portion substantially corresponding to said outer threading and to said axially outer end, having a greater wall thickness, and wherein said annular radial narrowing is determined by a different thermal shrinkage of said first and second axial portions following moulding of said first tubular connector with said first radial annular flange.

7. Device according to claim 1, wherein integral outer radial stiffening wings are arranged between said tubular connector and said second annular flange.

* * * * *

UNITED STATES PATENT AND TRADEMARK OFFICE
CERTIFICATE OF CORRECTION

PATENT NO.    : 6,086,762
DATED         : July 11, 2000
INVENTOR(S)   : Guala

It is certified that error appears in the above-identified patent and that said Letters Patent is hereby corrected as shown below:

<u>Column 6,</u>
Lines 38-40, cancel beginning with "2. Device according to "claim 1" to and including "polymers.", and insert the following claim:

2.    A transducer-protector device for biomedical heamodialysis lines, comprising a first tubular connector of the female Luer Lock type with a conical inner surface and an outer threading, intended to be connected to a tube of a haemodialysis equipment, a second tubular connector coaxial to said first tubular connector, said first and second tubular connectors being provided with respective first and second radial annular flanges for their mutual permanent sealed connection by ultrasonic welding, and a filtering membrane made of a permeable material defining an anticontamination sterile barrier interposed transversely between said first and said second tubular connectors and having a peripheral edge clamped between said radial annular flanges, wherein said second tubular connector with said second radial annular flange is formed by one piece of high rigidity moulded thermoplastic material, and wherein said first Luer Lock connector with said first radial annular flange is constituted by one piece of a moulded thermoplastic material having elasticity characteristics higher than those of said second tubular connector with said second radial annular flange, wherein said thermoplastic material having higher elasticity characteristics is selected in the class of polybutylenterephthalate polymers.

Lines 17 and 38, replace "tranducer" with -- transducer --.

Signed and Sealed this

Seventeenth Day of June, 2003

JAMES E. ROGAN
*Director of the United States Patent and Trademark Office*